(12) United States Patent
Horvath

(10) Patent No.: US 7,732,198 B2
(45) Date of Patent: Jun. 8, 2010

(54) DEVICE FOR THE REGENERATION OF TISSUE, SPECIFICALLY BONE REGENERATION BY MEANS OF CALLUS DISTRACTION

(75) Inventor: Domonkos Horvath, Jestetten (DE)

(73) Assignee: CelGen AG, Zug (CH)

( * ) Notice: Subject to any disclaimer, the term of this patent is extended or adjusted under 35 U.S.C. 154(b) by 642 days.

(21) Appl. No.: 11/598,044

(22) Filed: Nov. 13, 2006

(65) Prior Publication Data

US 2007/0059827 A1 Mar. 15, 2007

Related U.S. Application Data

(62) Division of application No. 10/678,059, filed on Oct. 6, 2003, now abandoned.

(51) Int. Cl.
*C12N 5/00* (2006.01)
*C12N 5/02* (2006.01)

(52) U.S. Cl. ........................ 435/325; 435/375
(58) Field of Classification Search ............... 435/325, 435/375
See application file for complete search history.

(56) References Cited

U.S. PATENT DOCUMENTS

| 5,306,305 | A | | 4/1994 | Lee |
|---|---|---|---|---|
| 5,676,699 | A | * | 10/1997 | Gogolewski et al. ..... 623/16.11 |
| 5,980,252 | A | | 11/1999 | Samchukov et al. |
| 6,030,218 | A | | 2/2000 | Robinson et al. |
| 6,280,760 | B1 | | 8/2001 | Meyer et al. |
| 2003/0083750 | A1 | | 5/2003 | Schulter |
| 2003/0104339 | A1 | | 6/2003 | Fromovich et al. |

FOREIGN PATENT DOCUMENTS

| DE | 197 25 788 A | | 1/1998 |
|---|---|---|---|
| FR | 2 753 366 A | | 3/1998 |
| WO | WO 97 31586 A | | 9/1997 |
| WO | WO 01/91663 | * | 12/2001 |
| WO | WO 03/045268 A1 | | 6/2003 |

* cited by examiner

*Primary Examiner*—Ruth A Davis
(74) *Attorney, Agent, or Firm*—Browdy and Neimark, PLLC

(57) ABSTRACT

The device incorporates a structurally stable membrane (4, 4', 34, 35) that incorporates a surface (15) to be bonded to a tissue to be regenerated, specifically a vital bone (2, 22, 38, 39). Means (9, 5, 6, 25, 36) are additionally provided whereby the membrane (4, 4', 24, 35) is movable for the regeneration with a certain pulling force and speed. According to the invention the membrane (4, 4', 24, 35) has, on its surface facing the tissue or bone, means (16) for the biological anchoring and adhesion for tissue or bone cells. These means (16) for the biological anchoring of tissue cells are specifically bone cells, protein molecules and/or osteoblasts (17), as well as indentations (45, 46, 48) and surface peaks (50) of the membrane.

12 Claims, 4 Drawing Sheets

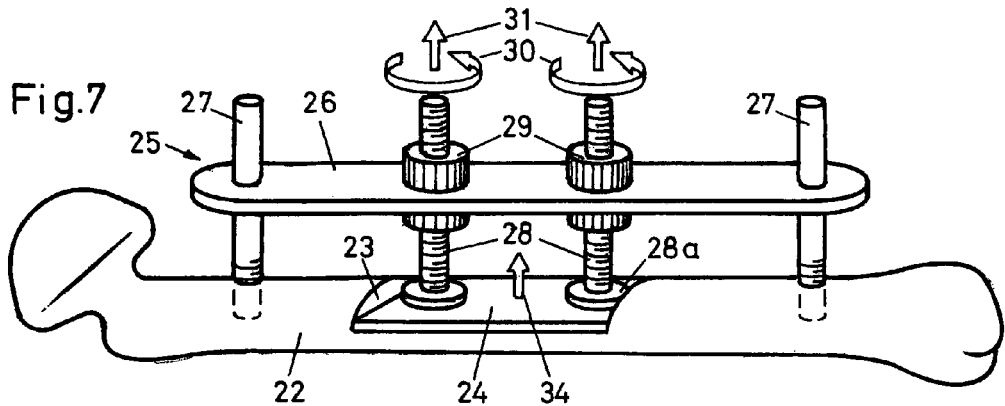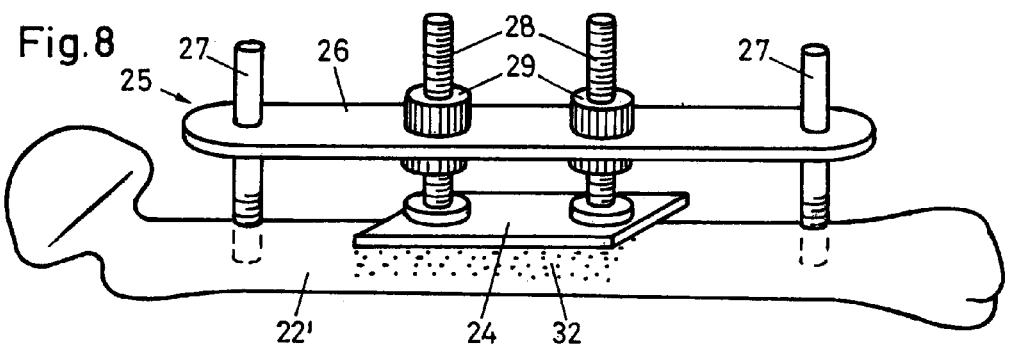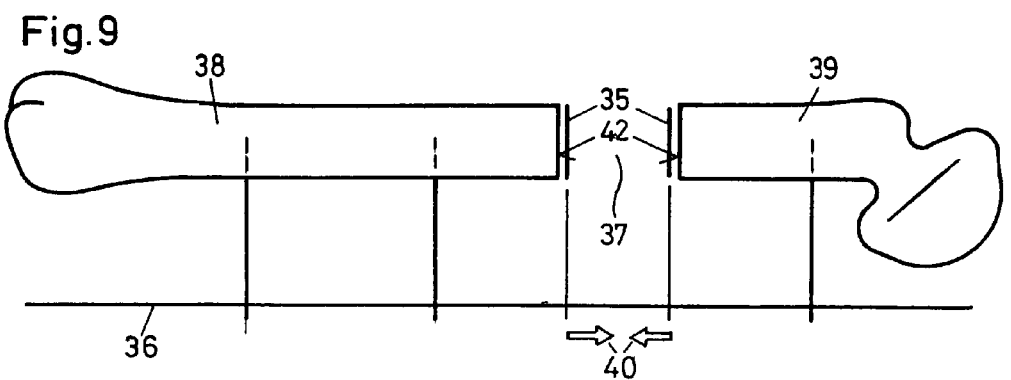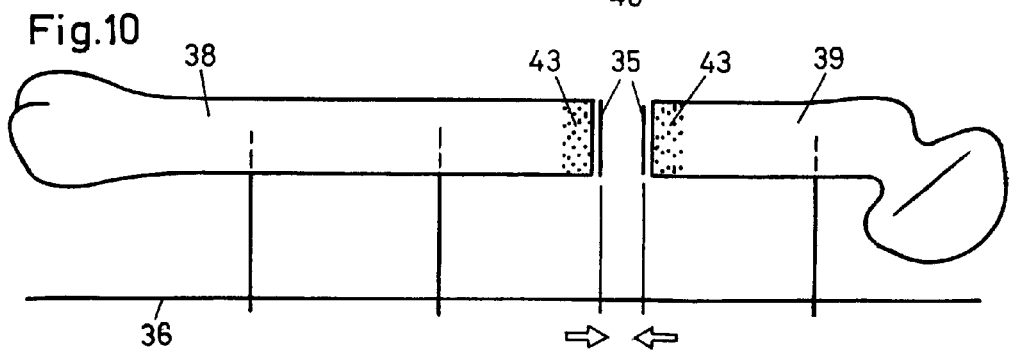

Figure 1:
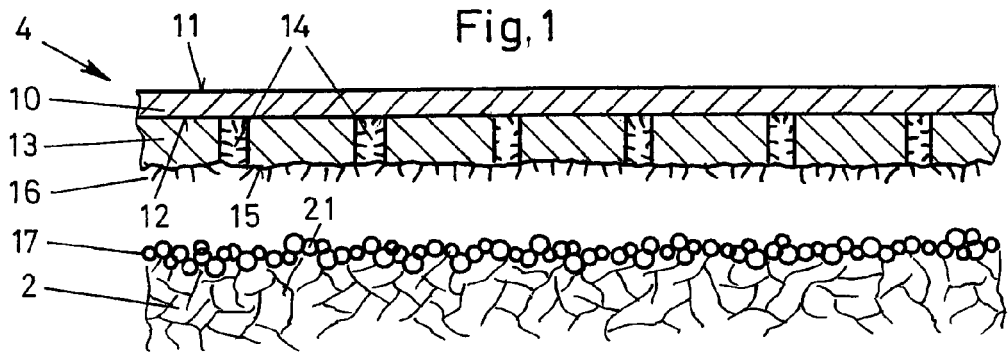

DEVICE FOR THE REGENERATION OF TISSUE, SPECIFICALLY BONE REGENERATION BY MEANS OF CALLUS DISTRACTION

The present application is a Division of prior application Ser. No. 10/678,059 filed Oct. 6, 2003 now abandoned.

The present invention is concerned with a device for the regeneration of tissue, specifically bone regeneration by means of callus distraction, having a membrane that is permeable for the exchange of nutrients at least for serum and structurally stable, incorporating a surface that is to be bonded to a tissue to be regenerated, specifically a vital bone, and having means whereby the membrane is movable for the regeneration. The invention is furthermore concerned with a membrane, as well as a process for tissue regeneration.

Methods for bone regeneration by means of callus distraction have been known for a long time. Callus distraction is used, for example, to build up the alveolar process. The formation of new bone is stimulated through progressive distraction of bone segments. In this manner a bone bed can be created in an alveolar process to receive an implant member. It is known that the formation of new bone occurs with a significant multiplication of osteoblasts, extracellular collagen and osteoids. Callus is the term for the temporary tissue that is formed in the course of a fracture consolidation. The osteoblasts, which have a diameter of approximately 20 micrometers, are responsible for the generation of bone tissue. The osteoblasts form an organic parent substance of collagen, which subsequently calcifies. Also known is the lengthening of extremities by means of callus distraction. In this process bone fragments are distracted approximately 1 millimeter per day. The distraction is followed by a consolidation phase during which the callus, which is soft during the distraction, hardens.

From the applicant's WO 01/91 663, a device for bone regeneration by means of callus distraction has become known in which a membrane is placed on the bone being regenerated and the formed callus is mechanically stressed. The device incorporates tension means whereby an adjustable tensile stress is exerted upon the membrane and a bone regeneration through callus distraction is thus induced. During the callus distraction a callus between the bone being regenerated and the membrane is stretched with this device. The membrane is moved at a certain speed, which may be 1 millimeter per day, for example. The speed is adjusted such that a soft callus can form during the distraction, which subsequently turns into a bone of satisfactory quality. If the speed of the distraction is too great, a callus of lesser quality is formed and, accordingly, a less sturdy bone. If the distraction takes place too slowly, the callus hardens and the membrane can no longer be moved, so that the distraction cannot be continued. The membrane is roughened on a surface facing the bone, to permit a bonding to a bone located underneath. A surface facing away from the bone is also roughened to prevent the membrane from becoming detached from a covering connective tissue.

From FR-2 753 366 A, a jaw implant has become known on which a resorbable membrane is fastened that covers a bone recess, which receives the implant.

It is the purpose of the membrane to enable a bone regeneration. A callus distraction, however, does not take place.

EP 0 475 077 reveals a membrane for bone regeneration that incorporates a resorbable or degradable polymer and/or polymeric ceramic material. The membrane serves to form callus on a bone. A callus distraction does not take place in this case either.

Although the exceptional importance of bone regeneration by callus distraction specifically in paradontology has been known for a long time, its use with the aid of the callus distraction has not found general acceptance in practice.

It is the object of the invention to create a device, a membrane, and a process that permits an even simpler and safer tissue regeneration and specifically bone regeneration by callus distraction. The invention is intended to specifically permit the bone regeneration in the field of paradontology.

The presented means for the biological adhesion of osteoblasts significantly improve the anchoring of the callus to the membrane. Due to this increased adhesion and corresponding anchoring of the callus to the membrane, there is a significantly greater certainty that the membrane will not be torn from the callus during the distraction. This also allows the callus to be stretched with the same forces as between two bone end pieces. The invention is not limited solely to the regeneration of bone tissue but it is suitable for any type of tissue in which cell proliferation and differentiation are triggered by biomechanical stimulus transfer on the cytoskeleton and tissue growth can be attained, like on an endothelium, for example.

The means for the biological adhesion of osteoblasts, according to an improvement of the invention, are anchor proteins that are fastened on the membrane. Protein molecules and particularly short-chain protein molecules are particularly suitable for the adhesion or anchoring of osteoblasts. The adhesion is based on an adhesion between the protein molecules and the osteoblasts. The protein molecules preferably extend over the entire surface facing the bone to be regenerated. In principle, other means, specifically organic molecules, are conceivable as well that ensure the above adhesion.

According to an improvement of the invention, provision is made for osteoblasts, which are anchored to said means for the biological adhesion, to be colonized on the surface of the membrane facing the tissue. The membrane in this embodiment variant is thus already colonized with osteoblasts. When the membrane is placed on a bone being regenerated, a callus, which is anchored to the membrane by adhesion, can form particularly quickly in this manner. The osteoblasts in this embodiment are preferably anchored to short-chain protein molecules by adhesion.

The means for moving the membrane and, hence, the distractors, according to an improvement of the invention, are mechanical pulling or pushing means. According to an improvement of the invention, the means for moving the membrane incorporate at least one magnet whereby a force and specifically a pulling force is exerted upon the membrane. The membrane is provided for this purpose with a ferromagnetic material, which is attracted by the magnet. The magnet is preferably fastened at a distance to the membrane, for example on a tooth or implant.

The invention is furthermore concerned with a membrane for tissue regeneration and specifically bone regeneration by means of callus distraction, wherein this membrane is permeable for the exchange of nutrients and incorporates a surface that can be placed on a tissue being regenerated, and moved for the regeneration. This membrane thus is characterized in that said surface incorporates means for the biological adhesion of osteoblasts.

The membrane, according to an improvement of the invention, is comparatively rigid so that it can exert a tensile stress onto a tissue substantially without deformation.

According to an improvement of the invention, the membrane incorporates a carrier that is made preferably of metal, for example of titanium. This carrier is preferably open-pored and forms a grid or net that is permeable, specifically for serum, for the renewal of the callus.

A particularly advantageous design of the membrane results when, according to an improvement of the invention, the carrier is provided on its surface with a film-like layer that is permeable for the exchange of nutrients. This layer also has disposed on it, in the region of the perforations in the carrier, means for the biological adhesion of osteoblasts. As a result, the entire surface of the membrane facing the bone being regenerated can be provided with said means for the biological adhesion. This results in a particularly high degree of adhesion of the callus on the membrane.

The invention is furthermore concerned with a process for tissue regeneration and specifically bone regeneration, wherein a membrane that is permeable for the exchange of nutrients is bonded to a tissue or vital bone being regenerated and moved for the regeneration. The process is characterized according to the invention in that the surface of the membrane facing the tissue incorporates means for the biological adhesion of osteoblasts and that the membrane is placed at the tissue location being regenerated so that cells of the tissue bond to said means of the membrane and that, to form new tissue, the membrane is subsequently moved away from the tissue at a certain speed.

According to an improvement of the inventive process, provision is made for the membrane to be provided with osteoblasts on its surface facing the tissue or bone, prior to its placement on the tissue or bone. These osteoblasts accelerate the callus formation when the membrane is placed on the tissue or bone. Additionally, a particularly high degree of adhesion of the membrane on the callus can be attained. During the distraction, the membrane is moved away from the bone at a speed of 0.5 to 2 millimeters per day, preferably approximately 1 millimeter per day. After the callus distraction is complete, a consolidation phase follows, during which the callus is transformed into bone.

For the regeneration or new formation of bone, a membrane is used according to the invention that appears to the vital bone being regenerated substantially like a second vital bone. The callus formation between the membrane and the vital bone being regenerated thus largely corresponds to a callus distraction between two vital bones.

Figure 2:
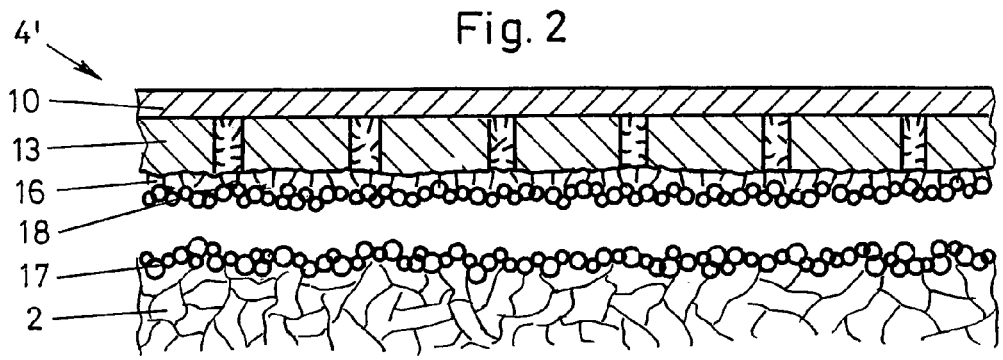
Figure 3:
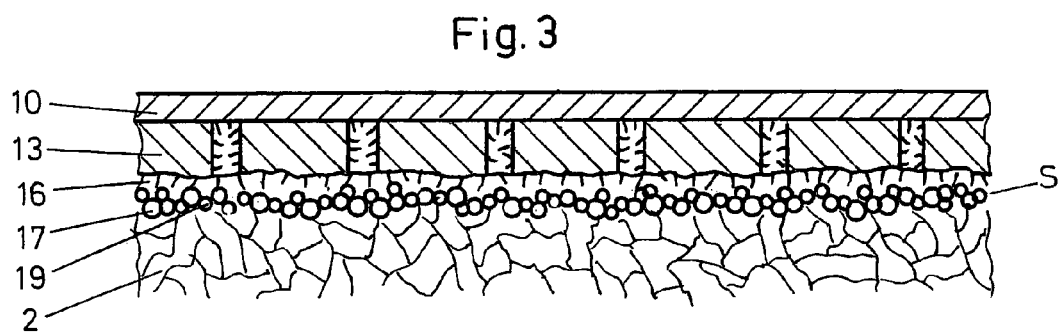
Figure 4:
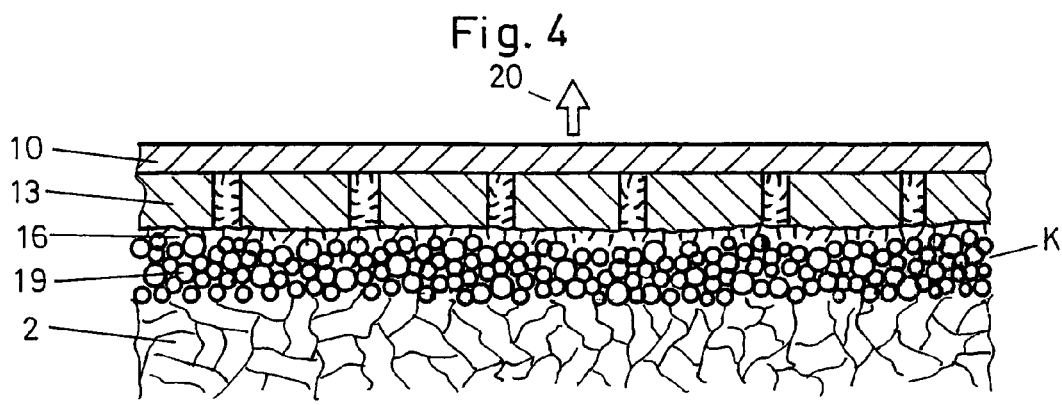
Figure 5:
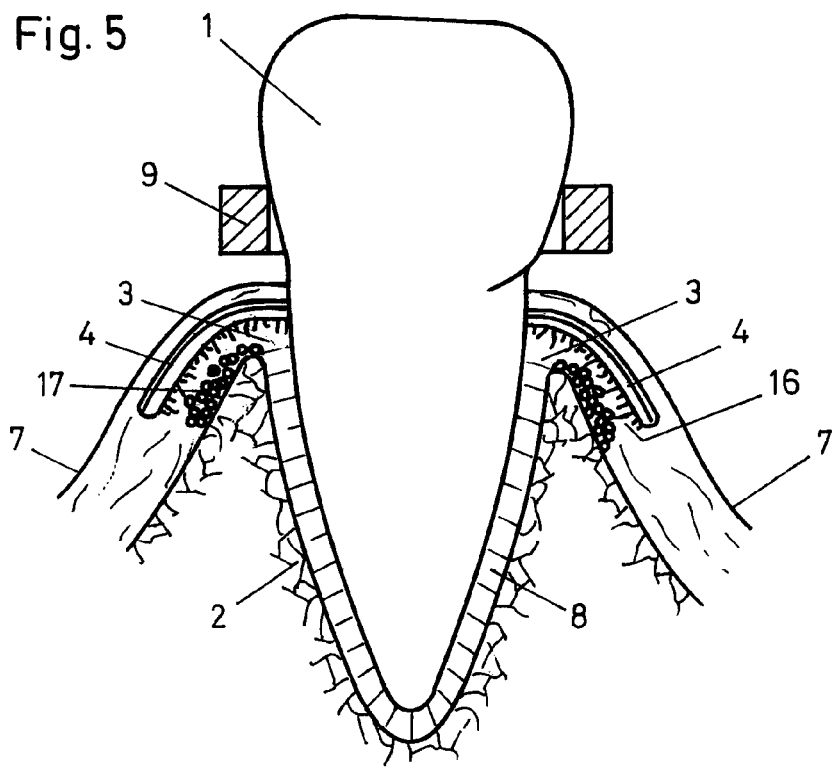
Figure 6:
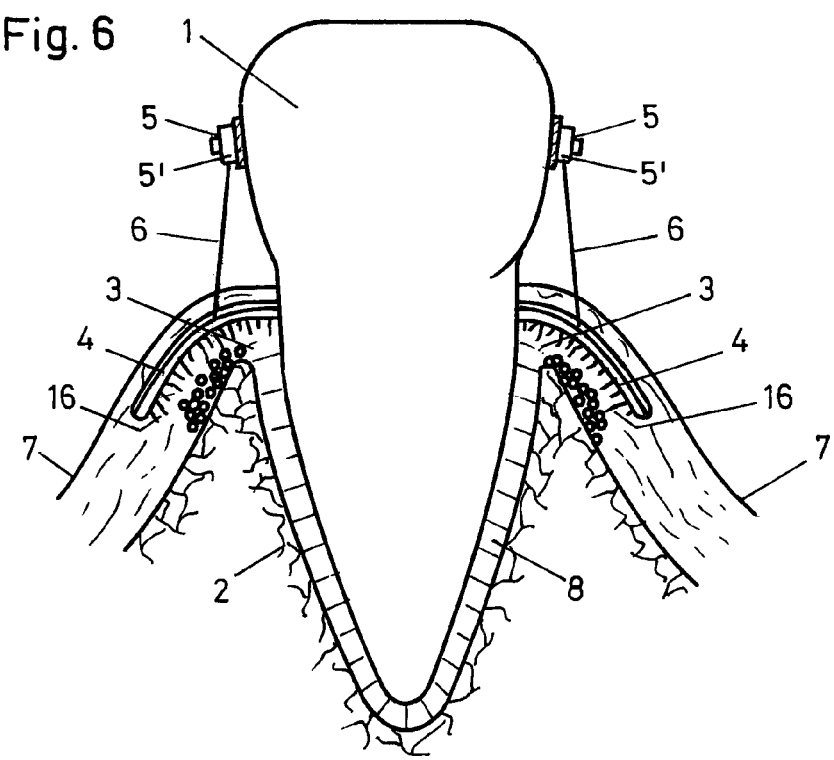
Figure 11:
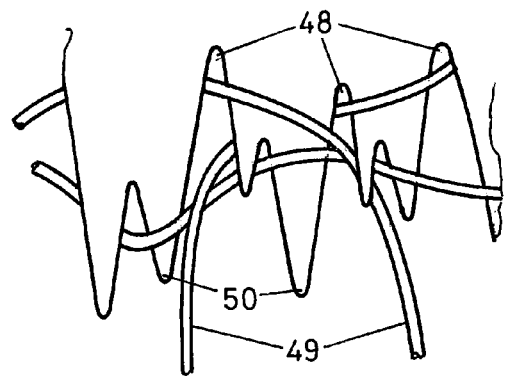
Figure 12:
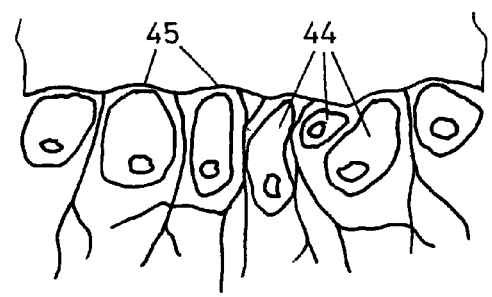
Figure 13:
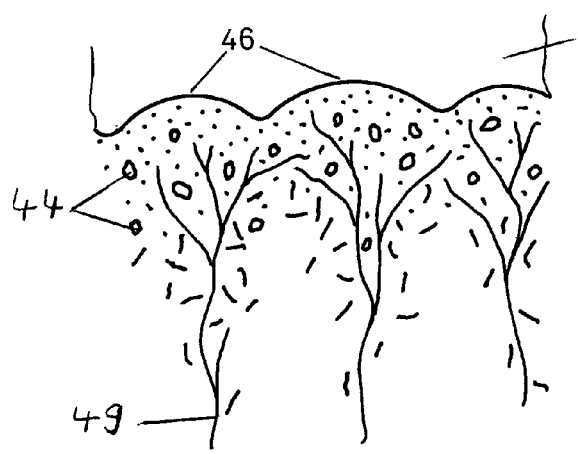
Figure 14:
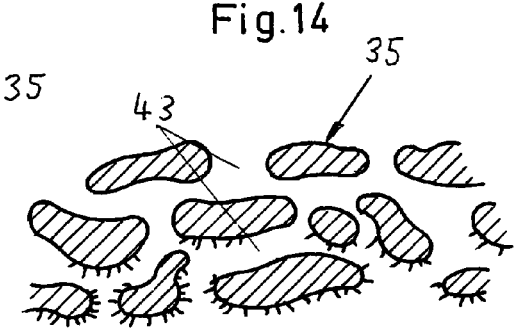

Embodiments of the invention will be explained in more detail below based on the drawings, in which:

FIG. 1 shows a schematic section through a vital bone being regenerated and an inventive membrane, FIG. 2 shows a schematic section through a vital bone and a membrane according to a variant, FIG. 3 shows a schematic section through a vital bone and an inventive membrane placed on same, FIG. 4 shows a schematic rendering according to FIG. 3, however, later in time after a callus has formed, FIG. 5 shows a schematic section through an inventive device for bone regeneration at the example of a bone regeneration in a tooth region, FIG. 6 shows a schematic rendering according to FIG. 5, however, with a variant of the inventive device, FIG. 7 shows a schematic dimensional view of an inventive device and a bone that is being regenerated with this device, FIG. 8 shows a view according to FIG. 7, however, after the completed regeneration, FIG. 9 shows a schematic dimensional view of an additional variant of the inventive device, and a bone that is being regenerated with this device, FIG. 10 shows a view according to FIG. 9, however, after the completed regeneration, FIG. 11-13 schematically show the different structures of the membrane, and FIG. 14 shows a schematic significantly enlarged section through the inventive membrane.

FIG. 1 shows a vital bone 2 that is to be regenerated on a surface 21 by means of callus distraction. The vital bone 2 is to be induced to form new bone specifically on the surface 21. The bone 2 is any vital bone that is suitable for a callus distraction; the vital bone 2, for example, is such a bone in a tooth region.

The membrane 4 has a flat, disk-like shape, which has been adapted to the surface 21 of the vital bone 2 and embedded in the gum. The membrane 4 may thus be shaped flat, as shown, or dimensional, as it is shown for example in FIGS. 5 and 6. The membrane 4 largely retains its shape and is stabilized, for example, with inserts or reinforcing ribs so that a force, especially a pulling force or pushing force can be exerted on it without significant deformation. Reference is made in this context to WO 01/91 663 A1 of the applicant's.

The membrane 4 has a flat layer 10 that is permeable for nutrient fluid and specifically for serum.

The layer 10 is specifically open-pored and has a thickness that is based on the structural requirements of the given application. This thickness is as a rule in the range of 0.1 to 2 millimeters. The pores, which are not shown here, are micropores that are wide enough to permit the passage of nutrients in a nutrient fluid. A substantial portion of these pores preferably has a diameter of less than approximately 500 micrometers.

The layer 10 is bonded along its surface to a carrier 13, which is a plate or grid or net, for example, of a suitable metal, specifically titanium. The carrier 13 incorporates a plurality of passages 14, which, in a plate-shaped embodiment, are perforations. These passages 14 permit the passage of nutrient fluid that is able to permeate the membrane 4 from a surface 11 and travel to a surface 15. The nutrient liquid is a serum in particular. The lower threshold of the diameter of these passages 14 is in the region of 5 µm to 25 µm. The carrier 13 may also be integrated into the layer 10. In principle, however, an embodiment is also conceivable wherein the carrier 13 does not exist and the layer 10 is stabilized by other suitable means. A stabilization by means of chemical surface hardening would be conceivable, for example.

The membrane 4 incorporates a surface 15 facing the vital bone 2. Applied to this surface 15 are means 16 for the biological adhesion of osteoblasts 17. These means 16 incorporate, for example, short-chain protein molecules that have 1 to 30 carbon atoms. The means 16 preferably extend over the entire surface 15 and additionally into the passages 14. Inside these passages 14 these means 16 are also applied on the inside of the layer. The means 16 in the region of the passages 14 are thus also disposed on an inner surface 12 of the layer 10. The means 16 are supplied with nutrients due to the open-pore design of the layer 10 and via the passages 14. In an embodiment in which the carrier 13 is not provided, the means 16 are applied directly to the surface 12.

FIG. 2 shows a membrane 4', which, in addition to the above characteristics, also incorporates osteoblasts 18 that adhere to said means 16 by adhesion. The osteoblasts 18 thus adhere, for example, to said short-chain protein molecules. The osteoblasts 18 may also be substituted or supplemented with other suitable cells.

The application of the membrane 4 or 4', respectively, and the process for the callus distraction using these membranes will be explained in more detail below.

To regenerate the bone 2 and induce it to form new bone, the membrane 4 or 4', respectively, is placed with its surface 15 on the vital bone 2 according to FIG. 3. Between the vital bone 2 and the membrane 4, a layer S is generated as a result, which is formed of osteoblasts 17 of the vital bone 2 and means 16 of the membrane 4. This layer S is provided with nutrients due to the porosity of the layer 10 and due to the passages 14. These nutrients stem, for example, from a tissue not shown here that is disposed above the membrane 4. It is now an essential feature that the osteoblasts 17, due to adhesion, quickly bond to the means 16, for example with short-chain protein molecules. This very quickly results in a comparatively high degree of adhesion of the membrane 4 to the vital bone 2. In the case of the membrane 4', the layer S additionally contains osteoblasts 18 of the membrane 4'. These osteoblasts 18, which are thus supplied to the vital bone 2 via the membrane 4', also improve the adhesion and accelerate the callus formation. The membrane 4' has on its surface 15 substantially the properties of a vital bone. The vital bone 2 thus can barely or not at all distinguish the membrane 4' from any other vital bone.

The layer S develops through multiplication of the osteoblasts 17 or 18, respectively, into a callus K that is shown schematically in FIG. 4. This callus K continues to be supplied with nutrients. Now the callus K is stretched for the callus distraction, which is known per se, in such a way that a force is exerted upon the membrane 4 in the directions of the arrows 20. Through this stretching a biological stimulus is provided to the callus K, which activates the osteoblasts 17 and 18 and also newly formed osteoblasts 19. The movement of the membrane 4 relative to the vital bone 2 thus induces a formation of new bone. The speed at which the membrane 4 is moved is preferably steady and amounts to 0.5 to 2 millimeters per day, for example. Due to said adhesion of the means 16 to the vital bone, a detachment of the membrane 4 during the callus distraction and hence during the movement of the membrane 4 is largely prevented. Said speed of the membrane 4 is adjusted such that the callus K can develop during the callus distraction without hardening. If the speed is too slow the callus K hardens and the membrane 4 can no longer be moved. When the membrane 4 has reached its intended end position it is not moved any further. During a subsequent consolidation phase the callus K converts into solid bone through mineralization. The development of the callus K during the callus distraction and consolidation phase can be monitored radiologically, for example, or by sonography.

FIGS. 5 and 6 show, by means of an example, an application of the inventive membrane 4 in the field of paradontology. The Figures show a tooth 1, a vital bone 2, paradontal tissue 3, as well as the paradontium 8. The membrane 4 is designed as explained above and may also be the membrane 4'. It is disposed below the gum 7 in the region of the vital bone 2, which is to be regenerated in the region of a lesion 3. Said means 16 are disposed on the underside of the membrane 4 or 4' facing the vital bone 2. As can be seen, the membrane 4 is shaped hood-like to match the shape of the bone 2. The callus distraction in this case takes place as explained above.

The membrane 4 is moved upward in FIG. 5 and thus away from the vital bone 2. To exert the required force onto the membrane 4, the tooth 1 has fastened to it a magnet 9 that pulls the membrane 4 upward. To permit a magnetic force to be exerted upon the membrane 4, it contains ferromagnetic substances. However, the membrane 4 may also contain particles in a suitable manner that are attracted by the magnet 9.

In the embodiment according to FIG. 6, the membrane 4 is pulled upward mechanically by pulling means 5 and the callus K is stretched in this fashion. The pulling means 5 incorporate, rotatably supported on the tooth 1, spools 5 onto which a thread 6 or suitable wire is wound, which is connected at a lower end to the membrane 4. The membrane 4 may be tensioned simultaneously with a plurality of such spools 5 and threads 6. In principle, however, the membrane 4 may also be pushed with suitable means from below.

FIGS. 7 and 8 show an additional embodiment of the inventive device, whereby a bone 22 is regenerated through callus distraction. The bone 22 incorporates a recess 23 that has resulted, for example, from the removal of a diseased bone segment or from an accident. This recess 23 causes a significant weakening of the bone 22 and it its now possible with the inventive device to regenerate this recess 23 with sturdy bone through callus distraction. For this purpose a membrane 24 is placed into the recess 23. The membrane 24 is plate-shaped and cut in such a way that, as is apparent from FIG. 7, it fits into the recess 23. The membrane 24 is made of titanium, for example and, to provide nutrients to the surrounding bone tissue, designed permeable at least for serum, for example open-pored. The membrane 24 is designed such that it is structurally stable. Specifically, it can be placed under tension without this resulting in any unfavorable deformation. Lastly, the membrane 24 is provided on its side facing the bone 22 with a bioactive layer or surface that ensures a comparatively quick and solid anchoring of the bone 22 on the membrane 24. This bonding takes place between the underside of the membrane 24 and the surface 33 of the recess 23 facing it. To permit a reliable callus distraction and formation of sturdy bone tissue, the underside of the membrane is executed bioactive, as mentioned above. Specifically, its underside is structured such that cells and specifically collagen cells can anchor to the membrane. The underside of the membrane 24 additionally incorporates preferably hydroxyl groups and/or amino groups that permit the chemical bonding to protein molecules, which form bridges between the membrane 24 and bone 22. These protein molecules form chains with 1 to 30 carbon atoms. The underside to be bonded of the membrane 24 preferably incorporates micro-structures, meso-structures and macro-structures. The meso-structures, according to FIG. 12, have indentations 45 of approximately 5-25 µ, to which cells 44, specifically osteoblasts, can dock. In the macro region, indentations 46 are provided, according to FIG. 13, of approximately 100 to 1,000 µ, into which particularly capillaries 47 can grow and anchor themselves. In the micro region, indentations 48 are provided according to FIG. 11, which, as a rule, are smaller than approximately 5 µ and into which, for example, fibrin strands 49 and protein molecules can engage and covalent chemical compounds —OH, —OH, OH can develop. Said indentations 48, due to the open-pore design of the membrane 24, are open toward the upper side of the membrane 24 and therefore contain serum, which can diffuse through the membrane 24. As is clearly shown in FIG. 11, surface peaks 50 are present in this region, which stand away vertically from the membrane surface and improve the anchoring, specifically of fibrin strands 49. The cells and tissue that grow into the recesses are thus always supplied with the necessary nutrients for the metabolism, which is particularly strong during the formation of tissue.

The membrane 24 is left in the starting position shown in FIG. 7 until the membrane 24 has bonded to the bone 22. Then the membrane 24 is moved upward in FIG. 7 and thus way from the bone 22. A pulling means 25 is provided for this purpose, which has a support plate 26 that is fastened to the bone 22 with two rod-shaped support means 27. On the support plate 26 two nuts 29 are supported, into which a threaded rod 28 is screwed in each case. These threaded rods 28 are rotatably connected at their lower end 28a to the membrane 24. When the two nuts 29 are turned in the direction of the arrow 30, a pulling force is exerted upon the membrane 24 in the direction of the arrow 34. This causes the membrane 24 to be moved upwards. Between the membrane 24 and bone 22 new bone tissue is formed, which is bonded to the membrane 24. The speed at which the membrane 24 is moved is typically approximately 1 mm per day.

When the membrane 24 reaches the position shown in FIG. 8, the recess 23 has filled in with newly formed bone tissue 32. This newly formed bone tissue 32 is still gelatinously soft, so that the membrane 24 can easily be removed. The bone tissue 32 is now transformed, during a subsequent consolidation period, into sturdy bone tissue, so that the regenerated bone 22' attains the desired strength.

FIGS. 9 and 10 show an additional variant of an inventive device for a callus distraction. This device incorporates two membranes 35 that, as a rule, may be designed identical to the above described membranes 4 and 24. The two membranes 35 have been inserted into an intermediate space 37 between two bone segments 38 and 39 and fastened to a pulling means 36 in such a way that they can be moved toward one another in the directions of the arrows 40. The membranes 35 are placed in a starting position shown in FIG. 9 onto the bone surfaces 42 in such a way that they bond to one of the membranes 35 in each case, as explained above. Once the membranes 35 are bonded to the respective bone segment 38 or 39, they are moved toward one another, as mentioned above, under utilization of a pulling force of a suitable speed. In the process, bone tissue 43 is generated, as indicated in FIG. 10. When the two membranes 35 rest against one another so that they cannot be moved any further, they are removed. The generated bone tissue 43 is still soft and can stabilize and grow together during the consolidation phase, so that a whole bone that is capable of carrying a load is ultimately obtained.

FIGS. 11 through 14 schematically show the surface structure of the membrane 35 in increasing enlargements. FIGS. 11 shows the surface peaks 50, to which the fibrin strands 49 of the tissue being regenerated can anchor. FIGS. 12 and 13 again show the anchoring of the cells 44 and fibrin strands 49 on the bioactive surface 15 of the membrane, and FIG. 14 shows the interconnecting pores 43 that permit the passage of serum to the tissue, as well as the bioactive surface 15 facing the tissue or vital bone. The surface peaks 50, the indentations 45, 46, 48, the above-mentioned osteoblasts 18 colonized on the surface 15, as well as the protein molecules disposed on the surface 15 and also mentioned above, are preferred means for the biological anchoring of the tissue or bone.

List of Reference Numerals

1 Tooth
3 Bone
4 Tissue
5 Membrane
6 Pulling Means
5' Spools
6 Thread
7 Gum
8 Paradontium
9 Magnet
10 Layer
11 Fibrin Strands
12 Surface
13 Carrier
14 Passages
15 Surface
16 Means
17 Osteoblasts
18 Osteoblasts
19 Osteoblasts
20 Osteoblasts
21 Surface
22 Bone
23 Recess
24 Membrane
25 Pulling Means
26 Support Plate
27 Support Means
28 Threaded Rods
28a Lower End
29 Nut
30 Arrow
31 Arrow
32 Bone Tissue
33 Surface
34 Arrow
35 Membrane
36 Pulling Means
37 Intermediate Space
38 Bone Segment
39 Bone Segment
40 Arrows
41 Bone Tissue
42 Capillaries
43 Interconnecting Pores
44 Cells
45 Indentations
46 Indentations
47 Capillaries
48 Indentations
49 Fibrin Strands
50 Surface Peaks
51 Means
S Layer
K Callus

What is claimed is:

1. A process for tissue regeneration, in which a membrane that is permeable to the exchange of nutrients is bonded to a tissue or vital bone to be regenerated, wherein a surface of the membrane facing the tissue or bone incorporates means for the biological adhesion of osteoblasts, and the membrane is placed onto the tissue or vital bone at a location to be regenerated, and the membrane is moved away from the tissue or vital bone for distraction at a speed of 0.5 to 2 mm per day.

2. The process according to claim 1, wherein the membrane, prior to placement on the tissue or vital bone, is provided with osteoblasts which are bound to the means for the biological adhesion of osteoblasts on the surface to be placed against the tissue or vital bone.

3. The process according to claim 2, wherein the membrane is moved away from the tissue or vital bone by means of at least one magnet or mechanical pulling means, at the speed of 0.5 to 2 mm per day.

4. The process according to claim 2, wherein the tissue is one of a type wherein cell proliferation and differentiation is initiated through bio-mechanical transmission of stimuli onto the cytoscleleton and growth or regeneration of tissue can be attained.

5. The process according to claim 1, wherein the membrane is moved away from the tissue or vital bone by means of at least one magnet or mechanical pulling means, at the speed of 0.5 to 2 mm per day.

6. The process according to claim 5, wherein the tissue is one of a type wherein cell proliferation and differentiation is initiated through bio-mechanical transmission of stimuli onto the cytoscleleton and growth or regeneration of tissue can be attained.

7. The process according to claim 1, wherein the tissue is one of a type wherein cell proliferation and differentiation is initiated through bio-mechanical transmission of stimuli onto the cytoscleleton and growth or regeneration of tissue can be attained.

8. The process according to claim 1, wherein the tissue regeneration is bone regeneration through callus distraction.

9. A process for tissue regeneration comprising:
   placing a membrane, that is permeable to the exchange of nutrients, onto a tissue or vital bone to be regenerated, to bond the membrane to the tissue or vital bone, and
   moving the membrane away from the tissue or vital bone for distraction at a speed of 0.5 to 2 mm per day,
   wherein the surface of the membrane facing the tissue or vital bone comprises osteoblasts attached to one or more compounds that biologically adhere to the osteoblasts, and is arranged so that the osteoblasts attach directly to the one or more compounds and not to the surface.

10. The process according to claim 9, wherein the one or more compounds are anchor proteins fastened on the membrane, or organic molecules that ensure adhesion of the osteoblasts.

11. The process according to claim 9, wherein the one or more compounds are short-chain protein molecules that have 1 to 30 carbon atoms fastened on the membrane.

12. The process according to claim 9, wherein the tissue regeneration is bone regeneration through callus distraction.

* * * * *